(12) United States Patent
Alzeer et al.

(10) Patent No.: US 10,548,764 B2
(45) Date of Patent: Feb. 4, 2020

(54) COOLING BED SYSTEM

(71) Applicant: MAZ Medical LLC, San Antonio, TX (US)

(72) Inventors: Abdulaziz Hamad Alzeer, Riyadh (SA); Troy Smith, Houston, TX (US)

(73) Assignee: MAZ Medical LLC, San Antonio, TX (US)

( * ) Notice: Subject to any disclaimer, the term of this patent is extended or adjusted under 35 U.S.C. 154(b) by 227 days.

(21) Appl. No.: 15/683,754

(22) Filed: Aug. 22, 2017

(65) Prior Publication Data

US 2018/0049911 A1 Feb. 22, 2018

Related U.S. Application Data

(60) Provisional application No. 62/378,076, filed on Aug. 22, 2016.

(51) Int. Cl.
*A61F 7/00* (2006.01)
*A61L 2/10* (2006.01)
*A61L 9/20* (2006.01)
*A61M 21/00* (2006.01)

(52) U.S. Cl.
CPC .......... *A61F 7/0085* (2013.01); *A61F 7/0053* (2013.01); *A61L 2/10* (2013.01); *A61L 9/20* (2013.01); *A61F 2007/0062* (2013.01); *A61F 2007/0064* (2013.01); *A61F 2007/0086* (2013.01); *A61F 2007/0093* (2013.01); *A61F 2007/0096* (2013.01); *A61M 21/0094* (2013.01)

(58) Field of Classification Search
CPC .................. A61F 7/0085; A61F 7/0053; A61F 2007/0093; A61F 2007/0062; A61F 2007/0086; A61F 2007/0064; A61F 2007/0096; A61L 2/10; A61L 9/20; A61L 2202/25; A61L 2/0047; A61M 21/0094
USPC .............................................. 5/284, 421–423
See application file for complete search history.

(56) References Cited

U.S. PATENT DOCUMENTS

| | | | | | |
|---|---|---|---|---|---|
| 959,743 | A | * | 5/1910 | Hoyt | A61H 33/06 4/530 |
| 1,038,394 | A | * | 9/1912 | Kruse | A61H 33/06 4/528 |
| 2,573,455 | A | * | 10/1951 | Koontz | A47C 21/048 5/284 |
| 3,565,072 | A | * | 2/1971 | Gauthier | A61G 10/02 128/200.16 |

(Continued)

*Primary Examiner* — Robert G Santos
*Assistant Examiner* — Myles A Throop
(74) *Attorney, Agent, or Firm* — Invention to Patent Services; Alex Hobson (57) ABSTRACT

A cooling bed system is configured to provide a cooling airflow around a patient suffering from heat exhaustion, heat stroke and or burns. A cooling bed system produces an airflow over a patient and preferably an airflow from both above and below the patient to more effectively and quickly cool the patient. A cooling bed system may also include a liquid dispenser that creates mist that is carried by the airflow to further cool the patient. A patient may be supported by a platform having a plurality of openings to allow airflow and mist to pass therethrough. A controller controls the airflow rate and/or temperature of the air, and may also control the liquid dispensing rate and/or temperature of the liquid as a function of an input from a temperature sensor to effectively and safely cool the patient.

21 Claims, 5 Drawing Sheets

(56) References Cited

U.S. PATENT DOCUMENTS

| | | | | |
|---|---|---|---|---|
| 3,703,173 | A * | 11/1972 | Dixon | A61G 10/04 128/200.14 |
| 3,789,228 | A * | 1/1974 | Bouchard | A61L 2/10 250/492.1 |
| 4,838,270 | A | 6/1989 | Donnerhack et al. | |
| 5,000,384 | A * | 3/1991 | Arnold | A47C 1/14 165/48.2 |
| 5,044,364 | A * | 9/1991 | Crowther | A47C 21/044 219/212 |
| 5,051,562 | A * | 9/1991 | Bailey | A61F 7/0085 219/483 |
| 5,227,095 | A * | 7/1993 | Curtis | F28C 1/02 261/111 |
| 5,337,960 | A | 8/1994 | Allen | |
| 5,387,181 | A | 2/1995 | Olsen | |
| 6,345,099 | B1 | 3/2002 | Bieberich | |
| 6,357,243 | B1 * | 3/2002 | Efron | G05D 23/1905 236/51 |
| 6,772,825 | B2 | 8/2004 | Lachenbruch et al. | |
| 6,871,367 | B1 * | 3/2005 | Beckles | A61G 7/0005 4/547 |
| 7,284,381 | B2 * | 10/2007 | Edwards | A62B 99/00 261/26 |
| 8,015,724 | B2 * | 9/2011 | Imahori | A45D 20/12 34/97 |
| 8,122,539 | B1 * | 2/2012 | Miranda | A47C 21/044 5/284 |
| 8,122,540 | B2 * | 2/2012 | Ardis | A47C 21/044 5/284 |
| 8,191,187 | B2 | 6/2012 | Brykalski et al. | |
| 8,881,998 | B1 * | 11/2014 | Sinkfield | A61F 7/0053 119/665 |
| 10,244,780 | B2 * | 4/2019 | Jung | A23L 3/3445 |
| 2003/0033666 | A1 * | 2/2003 | Hutsell | A61H 9/00 4/584 |
| 2004/0186537 | A1 * | 9/2004 | Heaton | A61F 7/0053 607/104 |
| 2005/0201910 | A1 * | 9/2005 | Shou | A61L 2/06 422/292 |
| 2005/0278863 | A1 * | 12/2005 | Bahash | A01K 1/0353 5/726 |
| 2010/0233019 | A1 * | 9/2010 | Al-Thallab | A61L 9/20 422/4 |
| 2011/0115635 | A1 * | 5/2011 | Petrovski | A47C 21/044 340/584 |
| 2012/0056102 | A1 * | 3/2012 | Stanley | G01J 1/0271 250/455.11 |
| 2012/0172959 | A1 | 7/2012 | Lachenbruch et al. | |
| 2012/0285459 | A1 * | 11/2012 | Sata | A61L 9/205 128/205.12 |
| 2015/0018903 | A1 | 1/2015 | Vapaavalta | |
| 2017/0136206 | A1 * | 5/2017 | Pillai | H04L 12/2816 |

* cited by examiner

COOLING BED SYSTEM

CROSS REFERENCE TO RELATED APPLICATIONS

This invention claims the benefit of U.S. provisional patent application No. 62/378,076, entitled Cooling Bed System and filed on Aug. 22, 2016; the entirety of which is hereby incorporated by reference herein.

BACKGROUND OF THE INVENTION

Field of the Invention

The invention relates to a cooling bed system for patients that are overheated or are suffering from a heat stroke.

Background

Heat stroke is a life-threatening condition characterized by a high core body temperature or more than 40° C. and a disturbed level of consciousness. It is a common occurrence for those that engage in physical activities, especially outdoor activity. Athletes, police and those in the military often are affected by overheating and heat stroke. The degree of tissue damage is dependent on the degree and duration of hyperthermia. Although several modes of therapy exist, no single treatment for these patients is universally accepted. In many situations, a person suffering with heat stroke is directed to lie down and elevate their feet. A cold compress may be applied to pulse points and/or to the person's head and they are encouraged to drink fluids, or an IV is introduced to hydrate the patient intravenously. It is important that the patient be hydrated as dehydration often accompanies heat stroke. In some situations, a person may be placed in an ice bath, however, this can interfere with hydrating the patient with an IV. There exist cooling blankets and beds having cooled liquid that is circulated through coils or a reservoir. The patient is however not in direct contact with the liquid and is cooled through conduction. In addition, a patient being in direct contact with a conductive reservoir cover or blanket will contaminate these articles requiring cleaning before use with another patient.

In addition, patients with burns often require rapid cooling and cooling that does not introduce any contaminates to the burns as they are very susceptible to infection.

SUMMARY OF THE INVENTION

The invention is directed to a cooling bed system that is configured to provide a cooling airflow around a patient suffering from heat exhaustion, heat stroke and or burns. An exemplary cooling bed system produces a flow of air over a patient and preferably an airflow from both above and below the patient to more effectively and quickly cool the patient. In an exemplary embodiment, a cooling bed system comprises a liquid dispenser that creates mist that is carried by the airflow to further cool the patient. A patient may be supported by a platform having a plurality of apertures therethrough to allow airflow and mist to pass therethrough. The platform may be removable and drawers for collection of liquid and bodily fluids can be removed from the frame for cleaning.

The cooling bed system may utilize a controller that receives sensor data from an air temperature sensor, liquid temperature sensor, patient temperature sensor and/or an enclosure temperature sensor, as well as liquid dispensing rate sensor and airflow rate sensors. The controller may utilize an algorithm that controls the air and/or liquid temperatures, the rate of airflow, the amount of liquid dispensed and combinations thereof to cool the patient in a safe and effective way. Cooling too rapidly may lead to shock and cooling too slowly may lead to tissue damage as well as brain damage. A controlled rate of cooling that is safe and effective is provided by the cooling bed assembly, as described herein.

An exemplary cooling system has an upper and a lower cooling portion that each have an air moving device. A filter or filters may be used to remove contaminates from the incoming airflow into the cooling bed system. The filters may be HEPA or ULPA rated to ensure that the airflow over the patient is clean and will not lead to infection. An air filter or air filtration system may be configured to be HEPA efficient thereby removing 99.7% of 0.3 µm or, larger particles, or ULPA efficient removing 99.999% of 0.1 µm or larger particles from the inlet air flow. In an exemplary embodiment, the air filter removes at least 99.95% of 0.3 µm or larger particles from the inlet air. In addition, an air temperature control device may adjust and control the temperature of the air, wherein the air is cooled or heated as required for effective and safe cooling of the patient. The airflow created by the upper and/or lower cooling portions may be laminar airflow the produces a controlled rate of cooling of the patient. In addition, the air moving devices, such as fans, of the lower cooling portion may be configured around the perimeter of the lower cooling portion to allow mist and bodily fluids to collect in drawers for easy cleaning.

An exemplary cooling system has an upper and a lower cooling portion that each have liquid misters to dispense a mist of liquid onto the patient. The liquid may be water, such as deionized water or filtered water to prevent any contamination. In addition, a liquid may comprise a medicant, disinfectant or some material, drug, or chemical that more effectively cools the patient or treats the patient. A medicant for a burn victim may include some disinfecting properties to prevent infection of their burns. A liquid may comprise a disinfectant, for example. A liquid reservoir may be used to store the liquid and conduits may extend from the liquid reservoir to the misters. A liquid temperature controller may be used to adjust and regulate the temperature of the liquid. In some cases, the liquid may need to be heated to ensure that the patient is not cooled too rapidly and in other cases the liquid may be cooled to provide a faster rate of patient cooling. The misters may dispense mist substantially over the patient, wherein at least 90% of the patient's body is exposed to mist. Again, a mist may be dispensed down from the upper cooling portion as well as up from the lower cooling portion. The misters on the lower cooling portion may be configured around the perimeter of the lower portion to allow liquid to collet in drawers for easy removal and cleaning.

An exemplary cooling system has one or more ultraviolet (UV) light sources that is configured to radiate UV light onto the patient. The UV light may be used to reduce the probability of infection and may also disinfect the air, water or mist of the system. A burn victim may have burns that can very easily become infected and ensuring that the air and mist are clean is very important. The UV light source may radiate UV light onto air conduits and/or a liquid reservoir, or liquid conduits, to disinfect the air and water. The air and liquid conduits and the liquid reservoir may comprise UV translucent or transparent materials to allow the UV light to pass therethrough for disinfection. For example, an inlet air conduit may extend along the top or bottom cooling portion and may be made out of a UV translucent or transparent plastic whereby the incoming airflow is exposed to the UV light prior to be directed onto the patient. Likewise, a liquid conduit for incoming liquid, inlet liquid conduit, or a dispensing conduit that extends to a mister may be made out of a UV translucent or transparent material and the liquid may be disinfected prior to being misted on a patient.

The upper cooling portion is offset vertically from the lower cooling portion by the frame and the gap therebetween provides an opening in the frame that allows a patient to be easily placed into and removed from the cooling bed assembly. In addition, the openings in the frame allows a caregiver to administer fluids, such as intravenously and check on the patient. The gap distance may be adjusted wherein the upper cooling portion can be lowered down along the frame to reduce the gap distance. This may be done after a patient is placed within the enclosure area on the platform. The gap distance may be reduced to about 30 cm or more, about 40 cm or more, or 50 cm or more and any range between and including the reduced gap distances provided. One or more curtains may be configured to close an opening in the, frame and to prevent or reduce ambient air from entering the enclosure area. Curtains may allow the airflow to be maintained without the influence of external airflow such as from wind or HVAC systems. The cooling bed system may maintain a positive pressure within the enclosure area from the airflow produced, by the air moving devices. As a result of this positive pressure, any openings in the enclosure will have airflow moving out from the enclosure, not into the enclosure. One of more of the curtains may roll up and down or slide up and down to allow entry into the cooling bed system and may be automatic having motor to actuate the curtain, for example.

The frame may be made out of a material that is resistant to water and/or liquid corrosion and may be stainless steel for example. The frame may have feet that are adjustable in height to enable easier access and location of a patient therein. In addition, the frame may be configured with wheels to allow the cooling bed system to be transported to a desired treatment location. An exemplary cooling bed system is powered by batteries or some other portable power generating device including, but not limited to, a generator, a fuel cell, a solar cell, and the like, thereby making the cooling bed system truly mobile.

A patient may be placed on a platform configured between the upper and lower cooling portions. The platform may rest on rails above the lower cooling portion and may be detachably attachable from the cooling bed system. The platform has a plurality of openings therein to allow airflow, mist and bodily fluids to pass therethrough. The platform may have screen like openings having an opening dimension, such as width, length or diameter of at least about 2 mm or more, least about 5 mm or more about 5 mm or more, about 10 mm or more, about 20 mm or more, about 50 mm or more and any range between and including the dimensions provided. Large openings are desired as it provides less resistance to flow. The platform may be made out of a material that does not soak in liquids, such as a polymer or metal. In an exemplary embodiment the platform consists essentially of plastic and has opening to allow air to pass therethrough but otherwise is non-porous to prevent bacteria growth. A platform may be made out of a solid material that has a smooth solid surface the does not absorb water or liquids and may comprise an antimicrobial material or coating, such as silver.

The summary of the invention is provided as a general introduction to some of the embodiments of the invention, and is not intended to be limiting. Additional example embodiments including variations and alternative configurations of the invention are provided therein.

BRIEF DESCRIPTION OF THE SEVERAL VIEWS OF THE DRAWINGS

The accompanying drawings are included to provide a further understanding of the invention and are incorporated in and constitute a part of his specification, illustrate embodiments of the invention, and together with the description serve to explain the principles of the invention.

DETAILED DESCRIPTION OF THE ILLUSTRATED EMBODIMENTS

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

In cases where the present specification and a document incorporated by reference include conflicting and/or inconsistent disclosure, the present specification shall control.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications and improvements are within the scope of the present invention.

Figure 1:
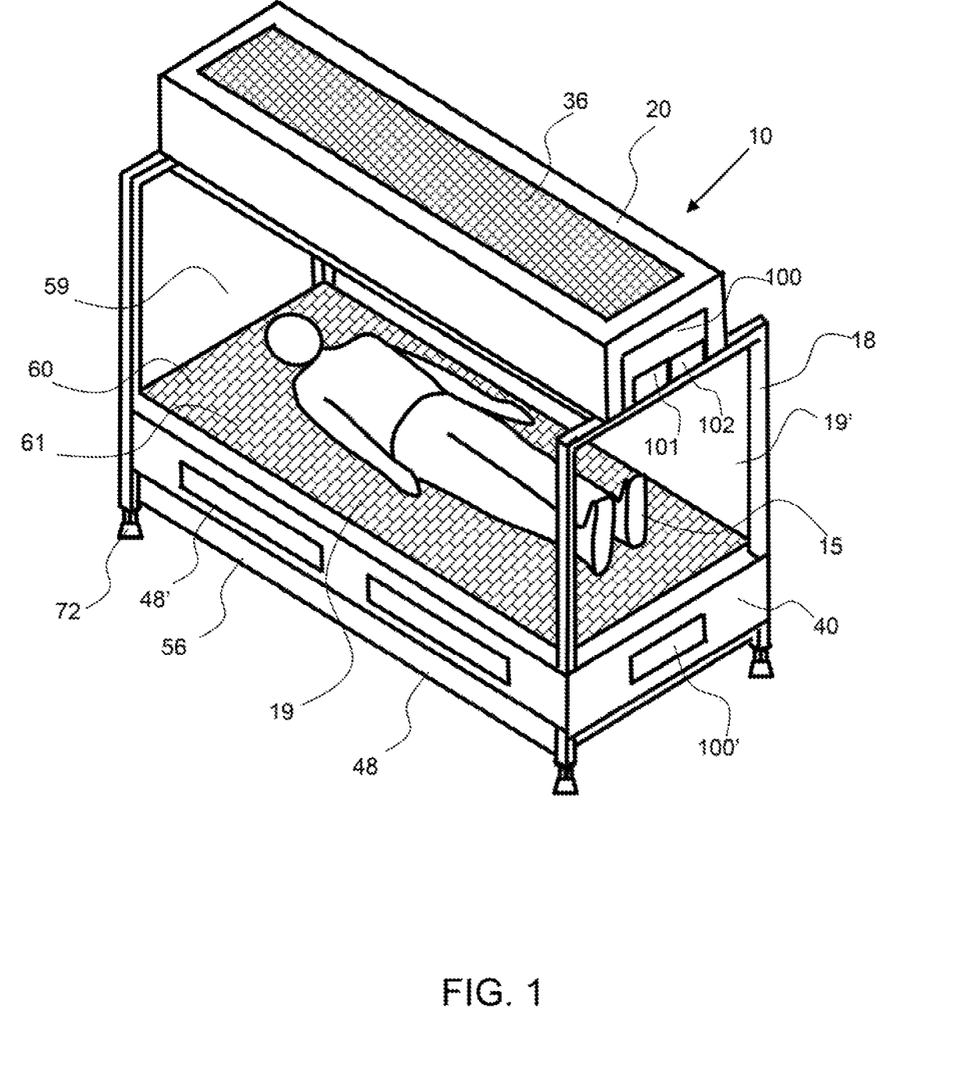
FIG. 1 shows a perspective view of an exemplary cooling bed system of the present invention.
Figure 2:
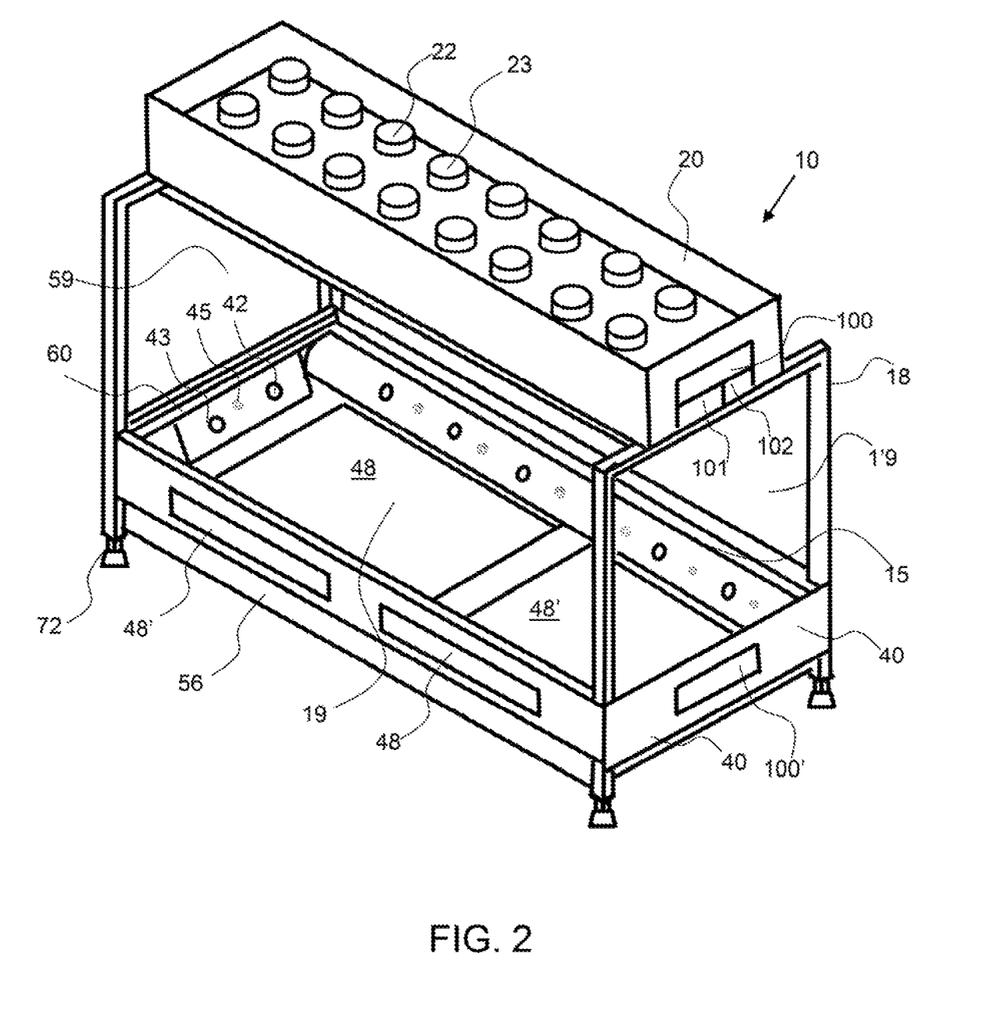
FIG. 2 shows a perspective view of the exemplary cooling bed system shown in FIG. 1 with the platform removed and the upper filter removed.

Referring to FIGS. 1 and 2, an exemplary cooling bed system 10 comprises a frame 18 having an opening 19 to receive a patient. The frame has vertical members that retain the upper cooling portion 20 up above the lower cooling portion 40. A patient 15 is lying on an air permeable platform 60, in the open area, or gap between the upper and lower cooling portions. The platform 60 has apertures 61 through the thickness to allow airflow and mist to easily pass therethrough. An upper filter 36 and lower filter 56 ensure that air drawn from the surrounding ambient air is filtered before being flushed over the patient. An upper and lower air temperature control device 100, 100' respectively are configured to control the temperature of the air and may comprises an air conditioner 101 and/or heater 102. A pair of collection drawers 48, 48' collect fluid including, mist and bodily fluids from the patient. The drawers allow the collected fluid and debris to be removed and the drawer can be cleaned between uses. The cooling bed system is on wheels 72 to allow it to be portable and mobile, wherein it can be moved to a desired treatment location, such as to an athletic event or race. As shown in FIG. 2, an exemplary cooling bed system 10 has the patient platform removed. The lower cooling portion 40 has a plurality of air moving devices 42, fans 43, that create an up-airflow from the lower cooling portion. The fans 43 are configured around the perimeter our outside edge of the lower cooling portion, thereby allowing liquid and mist to collect in the drawers 48, 48'. The drawers can be removed from the drawer insert locations. A plurality of misters 45 are also configured about the perimeter of the lower cooling portion to produce a mist that is carried by the up-airflow around the patient.

Figure 3:
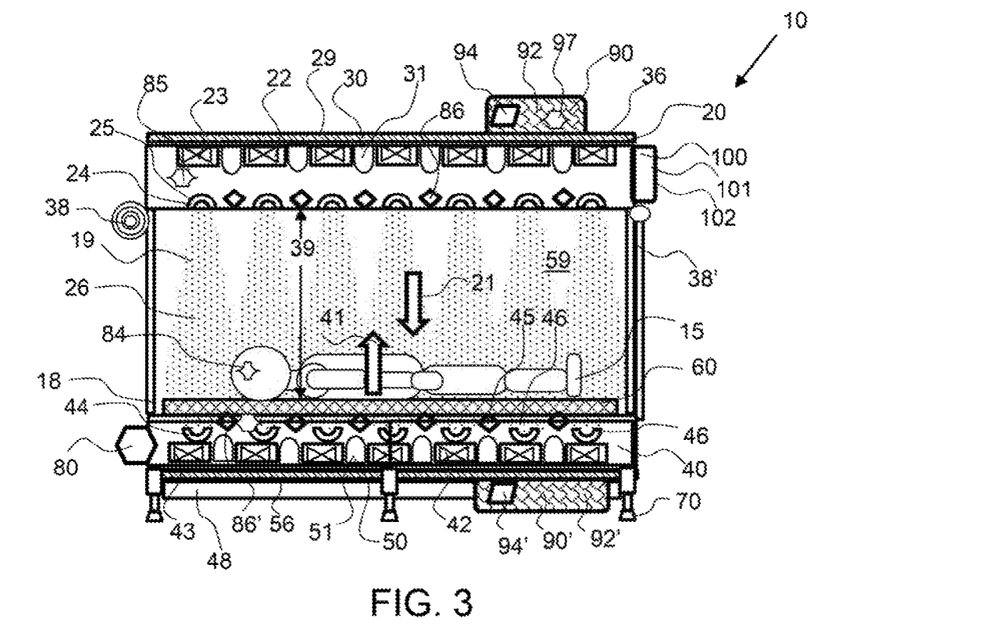
FIG. 3 shows a cross sectional side view of an exemplary cooling bed system of the present invention treating a patient with an airflow and mist from the upper and lower cooling portions.
Figure 4:
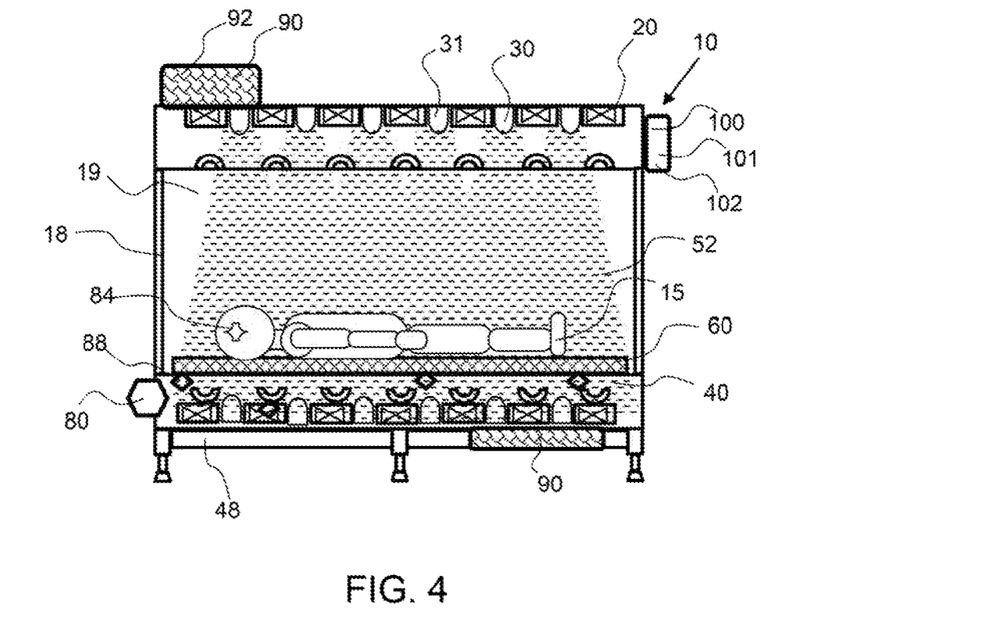
FIG. 4 shows, a cross sectional side view of an exemplary cooling bed system and UV light being radiated onto the platform from the above and below.

Referring to FIGS. 3 and 4, an exemplary cooling bed system 10 is being used to treat a patient 15 with a down-airflow 21 from the upper cooling portion 20 and an up-airflow 41 from the lower cooling portion 40, as indicated by the bold arrows. It is to be understood that the down and up airflows may not be exactly vertical in direction and may move in some offset angle to vertical. The patient is on the permeable platform 60 within the gap 39 between the upper cooling portion 20 and lower cooling portion 40. The patient is lying down on the platform 60 within the enclosure area 59. The curtain 38' on the right side of the frame 18 is down and the curtain 38 on the left side is rolled up. The curtains may be closed, thereby substantially closing off the openings 19 in the frame 18 to prevent disturbance of the airflow and contaminates from entering. A positive pressure may be formed that will prevent and/or reduce ambient air entry into enclosure area 59, the volume of space between the upper and lower cooling portions and within the frame 18 for treatment of a patient. The upper cooling portion 20 comprises a plurality of upper air moving devices 22, such as fans 23, that create the down-airflow 21. Likewise, the lower cooling portion 40 comprises a plurality of lower air moving devices 42, such as fans 43, that create the up-airflow 41. The upper cooling portion has an upper air filter 36 and the lower cooling portion 40 has a lower air filter 56 that are used to filter contaminates and particulates from the ambient air before entering the cooling bed system. These air filters ensure that the airflow produced by the upper and lower air moving devices, or fans, is clean and will not contaminate the patient in the event of any open wounds or through respiration. As described herein a patient with burns may be susceptible to contamination and infection and supply of clean air and liquid is important. An air temperature control device 100, comprising an air cooling device 101 and a heater 102 may be linked with the controller 80 and the controller may adjust the temperature of the air as a function of input from one or more sensors, such as a patient temperature sensor 84, air temperature sensor 85, or airflow sensor 86.

A plurality of upper liquid dispensers 24, or misters 25, create a mist 26 that is carried by the down airflow 21 over the patient. A plurality of lower liquid dispensers 44, or misters 45, create a mist 46 that is carried by the up-airflow 41 over the patient. One or more liquid reservoirs 90 may be configured to supply the liquid dispensers with a liquid 92, 92'. A liquid temperature control device 94, 94' may control the temperature of the liquid by either heating or cooling the liquid and a liquid temperature sensor 97 may provide sensory input to the controller 80. Air flow sensor(s) 86, 86' measure the airflow rates in the cooling bed system and delivery these readings to a controller 80. Upper air flow sensors 86 measure the airflow above the platform and lower air flow sensors 86' measure the airflow below the platform. The controller may then increase or decrease the airflow rates as a function of a temperature sensor reading, such as a patient body temperature sensor 84, or air temperature sensor 85. The temperatures sensor are coupled with the controller and a control program or algorithm may be used to control the airflow rates, amount of liquid dispensed and the temperature of the liquid dispensed. A liquid temperature control device 94 may be used to regulate the temperature of the liquid as directed by the controller.

A plurality of ultraviolet (UV) light sources 30, such as ultraviolet lamps 31, are configured in the upper cooling portion 20, and a plurality of ultraviolet (UV) light sources 50, such as ultraviolet lamps 51, are configured in the lower cooling portion 40 and are may be configured to decontaminate or disinfect the cooling bed system between. The UV lights may also be used to disinfect the air or liquid prior to being dispensed onto the patient. The UV light 52 produced by the UV light sources may be projected onto the surfaces of the upper and lower cooling portions including liquid and air conduits, the liquid reservoir as well as the frame and the patient platform. A UV light sensor 88 may measure the amount of UV light projected and this may be provided to the controller 80. An effective amount of UV light may be projected to clean and disinfect the unit. The exemplary cooling bed system 10 comprises drawers 48 for the collection of fluid and debris that may be removed and, cleaned and then placed back for decontamination.

Figure 5:
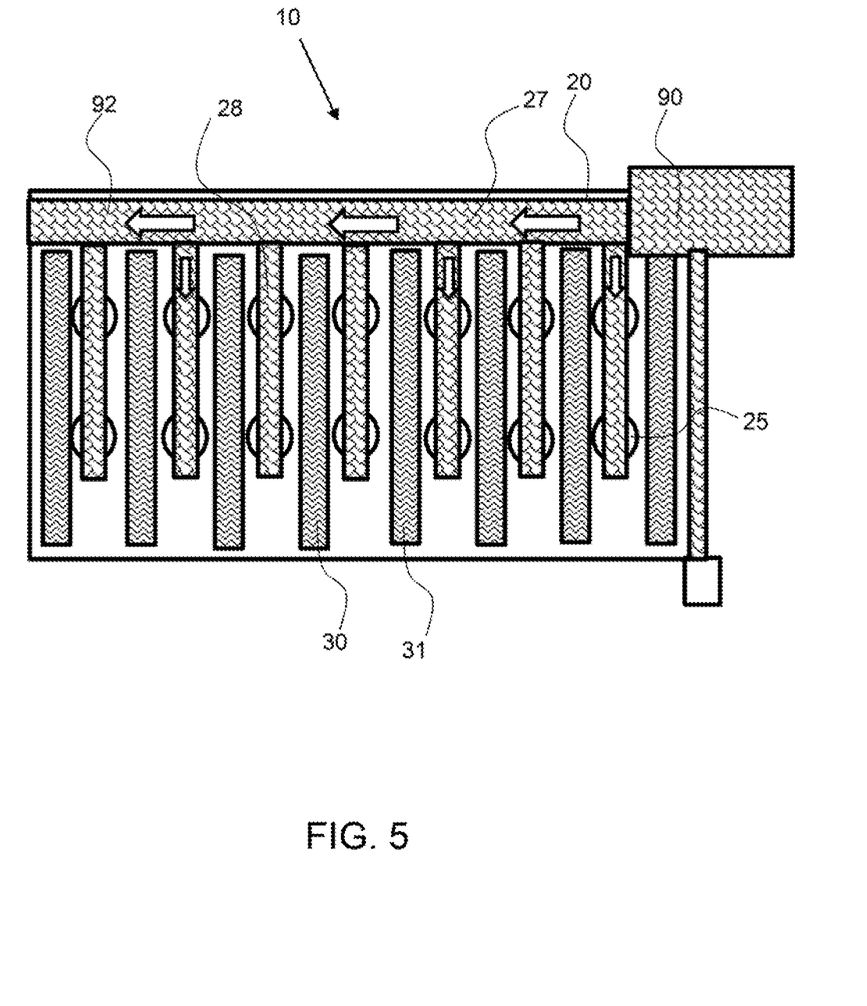
FIG. 5 shows a top view of an exemplary cooling portion having UV light sources configured between liquid inlet and delivery conduits to disinfect the liquid before being dispensed onto the patient.

As shown in FIG. 5, a plurality of UV light sources 30, such as UV lamps 31, are configured between the liquid deliver conduits 28, that extend to the misters 25. The liquid delivery conduits are made from a UV translucent material to enable the UV light to disinfect the liquid as it passes to the misters, Likewise, the UV light may disinfect the air in an airflow conduit before being directed onto the patient. The liquid 92 enters through a liquid inlet and is contained in a liquid reservoir 90 before being passed through the main liquid conduit 27, a conduit that extends to the delivery conduits 28. Again, the liquid reservoir, an inlet conduit, the main liquid conduit and the delivery conduits may all be made with or comprise a UV translucent or transparent material to allow disinfecting of the liquid.

Figure 6:
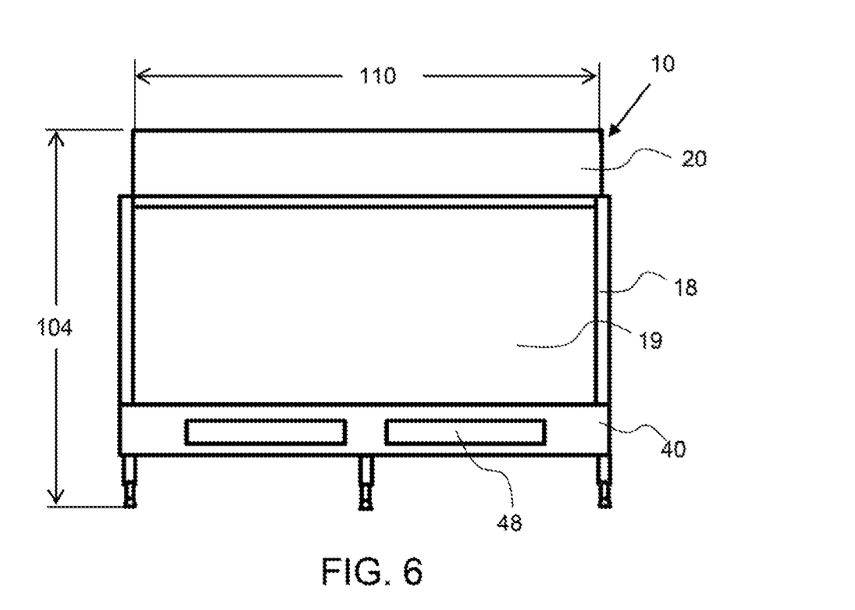
FIG. 6 shows a side view of an exemplary cooling bed system.
Figure 7:
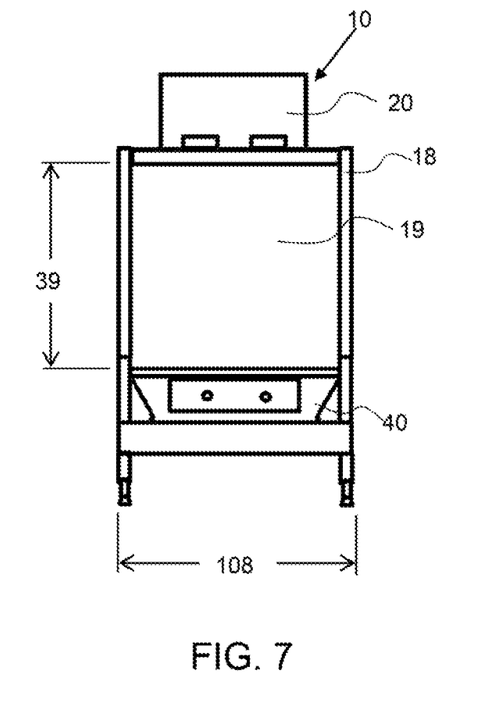
FIG. 7 shows an end view of an exemplary cooling bed system with the upper cooling portion in a raised configuration.
Figure 8:
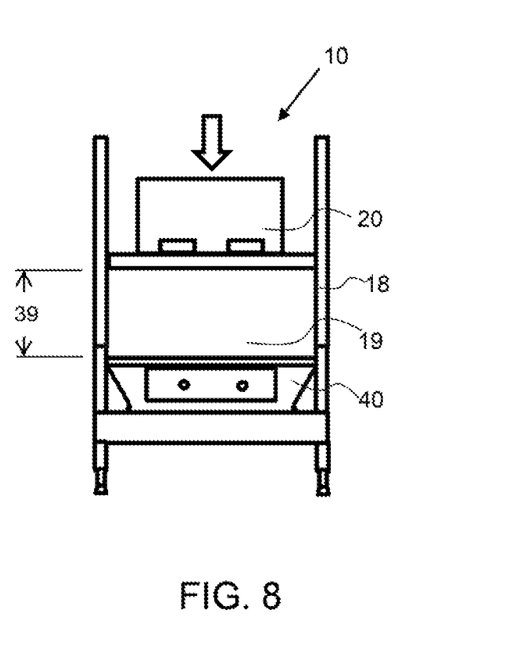
FIG. 8 shows an end view of an exemplary cooling bed system with the upper cooling portion in a lowered configuration.

FIGS. 6 to 8 show the general dimension of an exemplary cooling bed system 10, having a height 104, width 108 along the end, and a length 110. In FIG. 7, the upper cooling portion 20 is elevated and the gap distance 39 is larger than the gap distance in FIG. 8, wherein the upper cooling portion is lowered, as indicated by the large bold arrow. The upper portion may be lowered to provide more direct air flow or mist to the patient.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A cooling bed system comprising:
   a) a frame having an opening;
   b) an upper cooling portion comprising:
      i) an upper air moving device configured to create down-airflow that flows down;
      ii) an upper liquid dispenser configured to create a mist;
   c) a lower cooling portion comprising:
      i) a lower air moving device configure to create n up-airflow that flows up;
      ii) a lower liquid dispenser configured to create a mist;
   d) a patient platform configured between the upper and lower cooling portions;
      wherein a gap between the upper and lower cooling portion is configured to receive a patient through said opening in the frame;
      wherein the patient platform has a plurality of openings to allow mist from the upper and lower portions to pass therethrough;
   e) a controller that controls the rate of the upper and lower airflows.

2. The cooling bed system of claim 1, wherein the upper air moving device and lower air moving device each comprise a plurality of fans.

3. The cooling bed system of claim 1, wherein the upper liquid dispensing device and lower liquid dispensing device each comprise a plurality of misters.

4. The cooling bed system of claim 1, wherein the upper cooling portion comprises an upper filter, configured to filter out ambient air before entering the upper cooling portion.

5. The cooling bed system of claim 1, wherein the lower cooling portion comprises a lower filter, configured to filter out ambient air before entering the lower cooling portion.

6. The cooling bed system of clam 1, further comprising an ultraviolet light source configured to project ultraviolet into the cooling bed system.

7. The cooling bed system of claim 6, further comprising an ultraviolet light sensor that is coupled with the controller and wherein the controller activates and deactivates the ultraviolet light source as a function of an input from the ultraviolet light sensor.

8. The cooling bed system of claim 1, further comprising an ultraviolet light source in the upper and lower cooling portions,
   wherein a liquid conduit for the supply of liquid to the liquid dispensers is UV translucent; and
   wherein the ultraviolet light source projects ultraviolet light through the liquid conduit to disinfect the liquid before it is dispensed onto a patient in the cooling bed system.

9. The cooling bed system of claim 1, wherein the openings in the patient platform are at least 3 mm in dimension.

10. The cooling bed system of claim 1, wherein the patient platform is detachably attachable to the cooling bed system.

11. The cooling bed system of claim 1, comprising a temperature sensor that is coupled with the controller and wherein the controller adjusts the upper or lower airflow as a function of an input from the temperature sensor.

12. The cooling bed system of claim 11, wherein the temperature sensor is a body temperature sensor.

13. The cooling bed system of claim 11, wherein the temperature sensor is an air temperature sensor.

14. The cooling bed system of claim 1, wherein the lower cooling portion comprises a removable collection tray for collecting liquids and bodily fluids.

15. The cooling bed system of claim 1, further comprising a curtain configured to prevent ambient air from entering the cooling bed system wherein a gap between the upper and lower cooling portions is covered by said curtain.

16. The cooling bed system of claim 1, further comprising a liquid reservoir coupled with the liquid dispenser to provide a liquid for dispensing from the liquid dispensers.

17. The cooling bed system of claim 1, wherein the liquid is water.

18. The cooling bed system of claim 1, further comprising a liquid temperature control device that changes the liquid temperature before deliver to the liquid dispensers.

19. A cooling bed system comprising:
   a) a frame having an opening;
   b) an upper cooling portion comprising;
      i) an upper air moving device configured to create a down-airflow that flows down;
      ii) a plurality of upper liquid dispenser configured to create a mist;
   c) a lower cooling portion comprising:
      i) a lower air moving device configured to create an up-airflow that flows up;
      ii) a plurality of lower liquid dispenser configured to create a mist;
   d) a patient platform configured between the upper and lower cooling portions;
      wherein a gap between the upper and lower cooling portions is configured to receive a patient through said opening in the frame;
      wherein the patient platform has a plurality of openings to allot mist from the upper and lower portions to pass therethrough;
   e) a controller that controls the rate of the upper and lower airflows;
   f) an ultraviolet light source in the upper or lower cooling portion,
      wherein a liquid conduit for the supply of liquid to the liquid dispensers is UV translucent; and
      wherein the ultraviolet light source projects ultraviolet light through the liquid conduit to disinfect the liquid before it is dispensed onto a patient in the cooling bed system.

20. The cooling bed system of claim 19, wherein the upper and lower cooling portions comprise an ultraviolet light source and wherein each ultraviolet light source projects ultraviolet light through a liquid conduit to disinfect the liquid before it is dispensed onto a patient in the cooling bed system from the plurality of upper and lower liquid dispensers.

21. A method of cooling a heat stroke patient comprising the steps of:
   a) providing a cooling bed system comprising:
      i) a frame having an opening;
      ii) an upper cooling portion;
         an upper air moving device configured to create an down-airflow that flows down;
         an upper liquid dispenser configured to create a mist;
      iii) a lower cooling portion comprising:
         a lower air moving device configured to create an up-airflow that flows up;
         a lower liquid dispenser configured to create a mist;
         wherein a gap between the upper and lower cooling portions is configured to receive a patient through said opening in the frame;
      iv) a patient platform configured between the upper and lower cooling portions;
         wherein the patient platform has a plurality of openings to allow mist from the upper and lower portions to pass therethrough;
      v) a controller that controls the rate of the upper and lower airflows
   b) placing the heat stroke patient on the patient platform:
   c) activating the upper and lower air moving devices as well as the upper and lower liquid dispensers to create a flow of air and mist over the heat stroke patient;
   d) monitoring the heat stroke patient's temperature and controlling the upper and lower air moving devices as a function of the heat stroke, patient's temperature.

* * * * *